United States Patent
Haddix et al.

(10) Patent No.: US 7,594,511 B2
(45) Date of Patent: *Sep. 29, 2009

(54) DEVICE AND METHOD FOR PREVENTING UNWANTED ORAL ACTIVITY

(76) Inventors: Thomas R. Haddix, 1385 Maybee Rd., Monroe, MI (US) 48162; Christine Francis, 29401 Tamarack St., Flat Rock, MI (US) 48134

( * ) Notice: Subject to any disclaimer, the term of this patent is extended or adjusted under 35 U.S.C. 154(b) by 0 days.

This patent is subject to a terminal disclaimer.

(21) Appl. No.: 11/706,312

(22) Filed: Feb. 15, 2007

(65) Prior Publication Data

US 2007/0144536 A1 Jun. 28, 2007

Related U.S. Application Data

(63) Continuation-in-part of application No. 11/201,181, filed on Aug. 11, 2005, now Pat. No. 7,185,654.

(60) Provisional application No. 60/614,470, filed on Oct. 1, 2004.

(51) Int. Cl.
*A61F 5/56* (2006.01)

(52) U.S. Cl. ..................................... 128/848

(58) Field of Classification Search ................ 128/859, 128/861, 862, 848, 842, 844, 918, 921
See application file for complete search history.

(56) References Cited

U.S. PATENT DOCUMENTS

| | | | |
|---|---|---|---|
| 1,354,652 A | 10/1920 | Jefferies | |
| 2,574,623 A | 11/1951 | Clyde | |
| 2,867,212 A | 1/1959 | Nunn | |
| 4,459,105 A * | 7/1984 | Klein | 433/2 |
| 4,817,636 A | 4/1989 | Woods | |
| 4,825,881 A * | 5/1989 | Bessler | 128/859 |
| 4,883,072 A | 11/1989 | Bessler | |
| 5,425,635 A * | 6/1995 | Croll | 433/39 |
| 5,462,066 A | 10/1995 | Snyder | |
| 5,601,093 A | 2/1997 | Sheehan | |
| 5,613,942 A | 3/1997 | Lucast | |
| 5,642,737 A | 7/1997 | Parks | |
| 5,642,738 A | 7/1997 | Lilly | |
| 5,752,524 A | 5/1998 | Corcoran | |
| 5,806,525 A | 9/1998 | Pope | |
| D406,647 S | 3/1999 | Wagner | |

(Continued)

FOREIGN PATENT DOCUMENTS

| | | |
|---|---|---|
| JP | 2002-336286 | 11/2002 |
| JP | 2003-159269 | 6/2003 |
| JP | 2003-231638 | 8/2003 |

*Primary Examiner*—Patricia Bianco
*Assistant Examiner*—Camtu T Nguyen
(74) *Attorney, Agent, or Firm*—Richard C. Litman

(57) ABSTRACT

The device and method for preventing unwanted oral activity includes providing and selecting a perforated oral tape, drying the teeth, clenching the teeth, and applying the perforated oral tape to the upper and lower teeth of the user. The oral tape secures the upper and lower teeth together, thus preventing the unwanted oral activity. The oral tape is a flexible sheet of tear-resistant material having an adhesive back surface and a plurality of apertures defined therethrough. A pull tab is disposed on the front surface of the flexible sheet. The oral tape is adapted to adhere to the teeth of a user and secure the lower and upper teeth together so that the mouth of a user remains closed. The apertures in the tape allow air and saliva to pass therethrough. The unwanted oral activity may be snoring, smoking, snacking or the like.

3 Claims, 1 Drawing Sheet

U.S. PATENT DOCUMENTS

| | | |
|---|---|---|
| D407,495 S | 3/1999 | Savaiano |
| 5,884,628 A | 3/1999 | Hilsen |
| 5,893,365 A * | 4/1999 | Anderson .................. 128/848 |
| 5,921,240 A | 7/1999 | Gall |
| 5,941,247 A | 8/1999 | Keane |
| 6,076,526 A | 6/2000 | Abdelmessih |
| 6,089,232 A | 7/2000 | Portnoy |
| 6,170,485 B1 | 1/2001 | Orrico |
| 6,263,877 B1 | 7/2001 | Gall |
| 6,277,458 B1 * | 8/2001 | Dirksing et al. ............ 428/42.3 |
| 6,427,696 B1 | 8/2002 | Stockhausen |
| 6,439,238 B1 | 8/2002 | Brenzel |
| 6,467,485 B1 | 10/2002 | Schmidt |
| 6,604,528 B1 | 8/2003 | Duncan |
| D492,354 S | 6/2004 | Fujii |
| D492,781 S | 7/2004 | Vielhaber |
| 7,129,389 B1 * | 10/2006 | Watson ........................ 602/48 |
| 7,185,654 B2 * | 3/2007 | Haddix et al. ............... 128/848 |
| 2003/0068284 A1 | 4/2003 | Sagel |
| 2003/0075186 A1 * | 4/2003 | Florman .................... 128/869 |
| 2003/0149387 A1 | 8/2003 | Barakat |
| 2004/0089310 A1 | 5/2004 | Portnoy |
| 2004/0099275 A1 | 5/2004 | Zacco |
| 2004/0136927 A1 | 7/2004 | Kim |
| 2005/0089820 A1 * | 4/2005 | Allred et al. ................ 433/215 |
| 2009/0060958 A1 * | 3/2009 | Mello et al. ................. 424/401 |

* cited by examiner

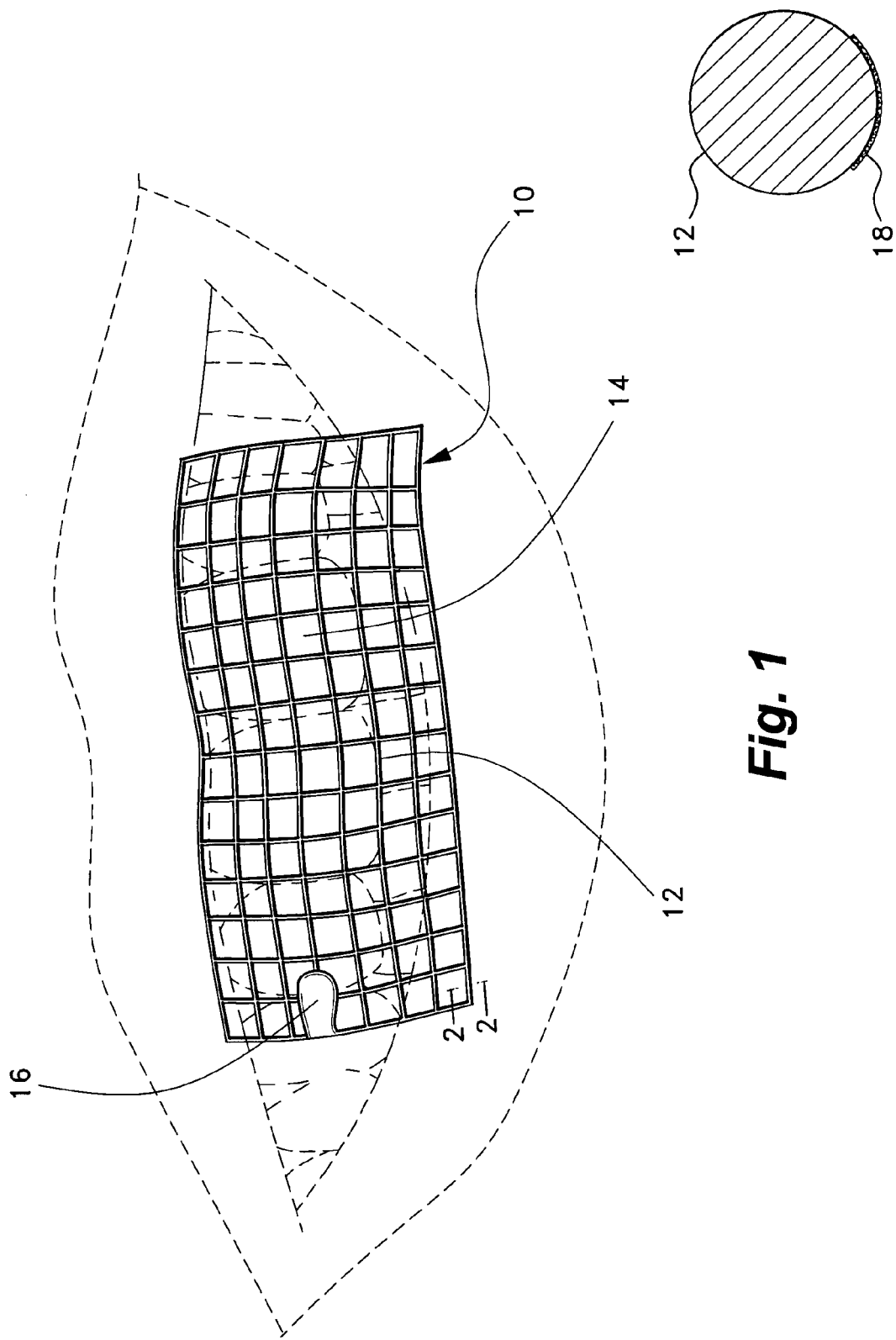

DEVICE AND METHOD FOR PREVENTING UNWANTED ORAL ACTIVITY

CROSS-REFERENCE TO RELATED APPLICATION

This application is a continuation-in-part of U.S. patent application Ser. No. 11/201,181, filed on Aug. 11, 2005, now U.S. Pat. No. 7,185,654 which claimed the benefit of U.S. Provisional Patent Application Ser. No. 60/614,470, filed on Oct. 1, 2004.

BACKGROUND OF THE INVENTION

1. Field of the Invention

The present invention relates to a device and method for keeping the mouth closed, and more particularly, to a device and method for preventing unwanted oral activity, such as snoring, smoking, snacking, or the like, using an oral tape that secures together the upper and lower teeth of a user during sleep to prevent snoring, or while awake as a deterrent to snacking, smoking, and the like.

2. Description of the Related Art

Snoring is caused when an individual breathes through the mouth during sleep in such a manner as to vibrate the uvula and/or soft palate in the interior of the mouth. Often, a snoring individual disturbs others who are within the vicinity. In addition, an individual who tends to snore during resting periods suffers from a lack of uninterrupted sleep in that he or she is awoken numerous times during the evening by the loud sounds of the snoring.

There have been many attempts to eliminate snoring during sleep. For example, there are surgical techniques available which permanently correct snoring problems encountered by individuals. However, most surgical procedures are complicated and invasive, sometimes requiring several hours to complete. While devices have been introduced which help prevent snoring without invasive surgery, they usually involve a mouthpiece that must be clamped.

A device for the prevention of snoring must be comfortable for the user to wear and provide for the transmission of air and saliva therethrough. Additionally, the device should be easily applicable and removable, and should be cost-effective to produce and purchase.

While various gums and dermal patches are available to help stop smoking, some persons may be allergic to such devices and desire some other approach to control smoking. Further, while diet pills may be effective in helping to lose weight or for appetite control, many persons may suffer adverse side effects from taking the pills and desire some other way to help deter between-meal snacking.

Thus, a device and method for preventing unwanted oral activity solving the aforementioned problems are desired.

SUMMARY OF THE INVENTION

The device and method for preventing unwanted oral activity includes providing and selecting a perforated oral tape, drying the teeth, clenching the teeth, and securing the perforated oral tape to the upper and lower teeth of the user so that the mouth of the user remains closed.

The device is an oral tape, which is a flexible sheet of tear-resistant material having an adhesive back surface and a plurality of apertures defined therethrough. A pull tab is disposed on the front surface of the flexible sheet. The oral tape is adapted to adhere to the teeth of a user and secure the lower and upper teeth together so that the mouth of a user remains closed while the user is asleep. The apertures in the tape allow air and saliva to pass therethrough. The adhesive is of a type proven safe for oral use.

These and other features of the present invention will become readily apparent upon further review of the following specification and drawings.

BRIEF DESCRIPTION OF THE DRAWINGS

FIG. 1 is an environmental, perspective view of a device for preventing unwanted oral activity according to the present invention.

FIG. 2 is a cross-section view along line 2-2 of FIG. 1.

Similar reference characters denote corresponding features consistently throughout the attached drawings.

DETAILED DESCRIPTION OF THE PREFERRED EMBODIMENT

The present invention relates to a device and method for preventing unwanted oral activity. As used herein, the term "unwanted oral activity" includes any activity that a person using the device and method wishes to avoid that involves opening the person's mouth, such as snoring, smoking, snacking, and the like. The method includes the selection of a perforated oral tape, generally designated as 10 in the drawings. The teeth or, at least, the area or areas of the teeth to which the tape must be applied are first dried with a towel or other suitable material. The teeth are then clenched together and the oral tape is positioned upon the upper and lower sets of teeth so that the upper and lower sets of teeth are secured and held firmly to one another. The oral tape thereby keeps the mouth closed during sleep in order to prevent the user from snoring, or while awake to deter smoking or snacking.

Referring to FIGS. 1 and 2, the oral tape 10 includes a flexible sheet 12 of tear-resistant material having an adhesive back surface 18 and a plurality of apertures 14 defined therethrough. A pull tab 16 is disposed on the front surface of the flexible sheet to facilitate removal of the tape 10 from the teeth of a user.

The flexible sheet 12 can be made from fabric, plastic, rubber, or any other suitable material. The flexible sheet can be any shape and size suitable for securing the upper and lower teeth together. For example, the sheet can be rectangular and have a width that is ¾ inches and a length that is approximately two inches, in order to fit within an average mouth. The back surface of the sheet 12 includes any suitable adhesive which can be adhered to and peeled away from the teeth effectively, and is further safe and hygienic for oral use. The tape may have a pattern of apertures similar to fishnet tape, but the size and number of apertures defined in the sheet 12 may vary within the scope of the invention. For example, the tape may have a checkerboard pattern of apertures such that approximately 50% of the flexible sheet 12 constitutes apertures 14 or open areas through which air and saliva may pass.

Since the oral tape is useful for keeping the mouth closed in order to prevent snoring, the oral tape may further be used as an aid to discourage snacking for those who are on a diet and also to discourage smoking for those who wish to refrain from smoking cigarettes.

It is to be understood that the present invention is not limited to the embodiments described above, but encompasses any and all embodiments within the scope of the following claims.
}

We claim:

1. A method for preventing unwanted oral activity, comprising the steps of:
   selecting an adhesive oral tape having perforations through a major portion of its surface area;
   clenching the upper teeth and lower teeth together; and
   securing the adhesive oral tape to at least four front upper and at least four front lower teeth, the adhesive oral tape fixedly securing the upper teeth to the lower teeth.

2. The method for preventing unwanted oral activity as recited in claim 1, further comprising the step of drying the upper and lower teeth before said clenching step.

3. The method for preventing unwanted oral activity as recited in claim 1, further comprising the step of utilizing a pull tab for removing said adhesive oral tape from the upper and lower teeth.

* * * * *